(12) United States Patent
Van Schijndel et al.

(10) Patent No.: US 9,710,551 B2
(45) Date of Patent: Jul. 18, 2017

(54) PERSONALIZED HEALING SOUNDS DATABASE

(75) Inventors: Nicolle Hanneke Van Schijndel, Eindhoven (NL); Armin Gerhard Kohlrausch, Eindhoven (NL); Werner Paulus Josephus De Bruijn, Delft (NL); Michel Marcel Jose Decré, Eindhoven (NL); Thomas Falck, Aachen (DE); Andre Melon Barroso, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 241 days.

(21) Appl. No.: 13/996,185

(22) PCT Filed: Dec. 21, 2011

(86) PCT No.: PCT/IB2011/055848
§ 371 (c)(1),
(2), (4) Date: Jan. 8, 2014

(87) PCT Pub. No.: WO2012/093305
PCT Pub. Date: Jul. 12, 2012

(65) Prior Publication Data
US 2014/0181127 A1 Jun. 26, 2014

(30) Foreign Application Priority Data
Jan. 7, 2011 (EP) ..................... 11150360

(51) Int. Cl.
*G06F 17/30* (2006.01)
*A61M 21/00* (2006.01)

(52) U.S. Cl.
CPC ....... *G06F 17/30761* (2013.01); *A61M 21/00* (2013.01); *G06F 17/30029* (2013.01); *G06F 17/30032* (2013.01); *A61M 2021/0027* (2013.01)

(58) Field of Classification Search
CPC ......... G06F 17/30772; G06F 17/30053; G06F 17/30144; G06F 17/30699; G06F 17/30761; G06F 17/30828; G06F 17/30867; G06F 17/30029; G06F 17/30032
USPC ......................................... 707/754
See application file for complete search history.

(56) References Cited

U.S. PATENT DOCUMENTS

| | | |
|---|---|---|
| 5,403,263 A | 4/1995 | Rodgers |
| 5,667,470 A | 9/1997 | Janata |
| 7,756,388 B2 * | 7/2010 | Plastina ............... G11B 27/105 386/241 |
| 8,490,123 B2 | 7/2013 | Bodlaender et al. |

(Continued)

FOREIGN PATENT DOCUMENTS

| | | |
|---|---|---|
| JP | H06186958 A | 7/1994 |
| JP | H06339354 A | 12/1994 |

(Continued)

*Primary Examiner* — Syed Hasan
*Assistant Examiner* — Saba Ahmed

(57) ABSTRACT

The invention relates to the field of music therapy. In particular the invention is related to a method for producing a personalized database of sounds and music tracks by filtering and combining personal and hospital databases of sounds which induces variations of the physiological state of a listener.

20 Claims, 2 Drawing Sheets

(56) References Cited

U.S. PATENT DOCUMENTS

| | | | |
|---|---|---|---|
| 2002/0037083 A1* | 3/2002 | Weare | G06F 17/30038 381/58 |
| 2006/0212478 A1* | 9/2006 | Plastina | G11B 27/105 |
| 2006/0218187 A1* | 9/2006 | Plastina | G06F 17/30029 |
| 2006/0242661 A1 | 10/2006 | Bodlaender et al. | |
| 2007/0176920 A1 | 8/2007 | Raijmakers et al. | |
| 2008/0301173 A1* | 12/2008 | Ryu | G06F 17/30056 |
| 2010/0145892 A1 | 6/2010 | Yang et al. | |
| 2010/0191037 A1 | 7/2010 | Cohen et al. | |
| 2010/0312042 A1 | 12/2010 | Anderson et al. | |
| 2012/0290621 A1* | 11/2012 | Heitz, III | G06F 17/30772 707/780 |

FOREIGN PATENT DOCUMENTS

| | | |
|---|---|---|
| JP | 2004154334 | 6/2004 |
| WO | WO0220080 | 3/2002 |
| WO | WO2004107757 | 12/2004 |

* cited by examiner

PERSONALIZED HEALING SOUNDS DATABASE

FIELD OF THE INVENTION

The invention relates to the field of music therapy. In particular, the invention is related to a method for producing a personalized database of sounds and music tracks which induces variations of the physiological state of a listener.

BACKGROUND OF THE INVENTION

Researches show that sounds, in particular music, can have a beneficial effect on the listeners. Generally, listeners by listening to a specific music track may increase their level of relaxation and reduce anxiety, pain, and therefore the consumption of sedatives and pain killers, such as morphine.

Certain type of music or nature sounds may be considered as having a healing effect on listeners by reducing anxiety, stress and pain.

Undoubtedly, the positive effect of specific sounds and sound stimulation on people suffering different disease has been demonstrated.

For example, patients of Intensive Care Unit (ICU) generally experience delirium which is probably the single most common acute disorder affecting ICU patients. Delirium is an acute confusional state which is common to severe neuropsychiatric syndrome and produces attentional deficits, severe disorganization of behavior, cognitive deficits and psychotic features such as hallucinations and delusions. Exposing ICU patients to specific sounds and music tracks may prevent delirium and improves patients' visual and acoustic conditions, i.e. avoiding loss of the patients' sense of place and time.

However, the positive influence of particular sounds or music stimuli is way more effective if the patient's personal preferences are taken into account.

Indeed, one of the key issues is how to account for personal differences among patients, due to their different taste and preferences. For example, a music track with slow tempo may be disliked by a listener and it will not induce on him a relaxing effect, while on other listeners the very same music tracks may induce the opposite effect.

US 2010/0191037 relates to the use of music in connection with cancer therapy. The method modulates the mood in a person by filtering a play list of music tracks creating a progressive modulation of mood from the initial mood to the target mood, by exposing the listener to that play list of music tracks.

US 2007/0176920 describes a system for providing a personalized experience to a person in a medical environment. However, the personalized experience is obtained through a limited selection within the hospital database content and the only interaction of the person is a manual selection between the different content that the hospital database provides.

The inventor of the present invention has appreciated that an improved method for producing a personalized sounds database is of benefit, and has in consequence devised the present invention.

SUMMARY OF THE INVENTION

It would be advantageous to achieve a personalized database of beneficial sounds, such as healing sounds. It would also be desirable to enable a user to access a personalized database of healing sounds.

In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect, the invention relates to a computer-implemented method of producing a personalized sounds database, the method comprising: determining preferred values of sound features of elements of a first database comprising elements, such as sounds, thereby creating a first filter; applying the first filter to a second database comprising elements, such as sounds, thereby producing a filtered second database.

Elements may be sounds, which is used herein as synonymous of music excerpt, music tracks, songs or radio programs, nature sounds, e.g. birds singing or waterfalls noise. Some elements may be directly recorded by the owner of the database, e.g. during an outdoor trip to a forest. For the purpose of this application sounds is referred herein also as music tracks.

A database comprising elements, such as sounds may be any music or sounds library in any form. The database may be recorded on any type of support, such as a memory stick, a computer hard disk, smart music player or smart phone memory. The database may also be a remote library accessible through specific software, for example a playing list accessible through the internet.

The invention describes a method for producing a personalized sounds database by creating a personal filter, referred to as first filter, comprising determining preferred values of sounds features of elements of a personal database comprising elements, such as sounds, referred to as first database and applying this personal filter to a general database, referred to as second database so as to produce a general database comprising personal characteristics, referred to as filtered second database.

The personal database may be a patient collection including patient favorite sounds. The personal database of sounds may be a database provided by the patient or compiled by his relatives on behalf of the patient by selecting songs from another database, e.g. the general database.

The general database may be a collection of sounds, including healing sounds, such as a music library of a hospital. Based on the patient collection, the personal musical preferences of the patient are determined. These personal preferences are used to refine the personal filter.

The wording healing is used as referred to its beneficial effect on people who are exposed to specific sounds, also referred to as listeners. Therefore, the wording healing, for the purpose of this application should not be limited to the general definition of curative, but may also have the meaning of preventing the occurrence of a negative effect on listeners.

Sound features are referred herein also as characteristics of the element.

For example, the sound features may be, in some embodiments, tonality, percussiveness or spectral bandwidth.

In some other embodiments the sound features may be the perceived tempo of the elements.

In some embodiments the computer-implemented method according to the first aspect further comprises: applying a second filter to a first database comprising elements, such as sounds, thereby producing a filtered first database.

The invention describes a method for producing a personalized sounds database by applying a filter, also referred to as second filter to a personal database, also referred to as first database so as to produce a filtered database containing personal elements, referred as to filtered first database.

In some embodiments the computer-implemented method further comprises: combining the filtered first database with the filtered second database, thereby providing the personalized sounds database.

This invention describes also a method to personalize a sounds database by combining at least two filtered databases so as to produce a personalized and therefore improved database of sounds.

The personalized database is also referred herein as improved database as it has improved features compared to the first and second database. Indeed, by combining filtered sounds of the first and second database, e.g. personal sounds having healing effects to the listener and healing sounds having favorite characteristic features of the listener, an improved database is obtained.

Combining filtered first and filtered second database is herein defined as combining the elements in the two filtered databases.

The combination of the filtered first database and filtered second database provides a personalized sounds database where filtered personal elements from the filtered first database are combined to filtered elements from the second database to achieve a personalized database.

The combination of the filtered databases can be done by simple collection into a common database of the elements included in the two filtered databases. In some embodiments the combination of the elements of the two filtered databases may be done by giving different weights to different elements.

The combination of the filtered first database and filtered second database is so that sounds from the first database, e.g. the patient collection, having perceived tempi producing desired effect on the listeners, and sounds from the second database, e.g. music library of an hospital, having characteristics, e.g. tonality, percussiveness, spectral bandwidth, similar to the sounds in the first database, are combined into a personalized database.

The combination of the filtered databases can be done by simple collection into a common database of the songs included in the two filtered database. In one embodiment the combination of the songs of first database can be weighted. For example, songs from the first database having a higher healing character may have a higher weight in this combination.

Once the elements from the two different filtered databases are combined, the personalized database can be accessed and sounds within the database can be played randomly or with a pre-determined order. Any modification regarding re-producing and accessing elements within a database is within the person skilled in the art.

In some other embodiments the first database is a database comprising user favorite sounds.

Favorite sounds may be easily identified by the user within his/her own collection of sounds on the basis of the desired effect that the user wants to achieve.

For example, if the listener would like to relax he/she may choose a collection of music tracks which are his favorite in light of the relaxing state he would like to achieve. This may include soft tunes and/or slow tempi. Alternatively, a different favorite collection may be preferred if an active state would like to be achieved. This may include high rhythm and/or fast tempi.

Favorite sounds may be personally chosen or chosen by relatives within a personal database or within other databases.

In some embodiments, the first filter comprises a digital signal processing algorithm, the digital signal processing algorithm, when applied to the second database, selects, from the second database, those elements having features with values similar to the preferred values of the sound features of the elements of the first database.

The invention describes a computer-implemented method wherein the first filter or personal filter is a digital signal processing algorithm which determines the preferred sound features of the first or personal database of sounds. When the filter is applied to the second database it selects from the second database those elements, such as sounds, which are closely related, by means of sounds features similarity, to the preferred sounds features of the personal database.

The first filter or personal filter may be a digital signal processing algorithm which determines the musical preferences of the owner of the database, i.e. the first database, by analyzing the sound features, i.e. the sound characteristics of the database such as a sounds collection, and filters out from a general database those elements having similar sound features. By applying the first filter, a personalized selection among a general database, i.e. the second database, is made.

For example, for each sounds of the first database, e.g. for each song in the personal collection, sound features, such as tonality, percussiveness, rhythm and spectral bandwidth, are determined. For example, the percussiveness feature may be evaluated by approximating sounds with a three phase envelope known as Attack, Decay/Sustain, and Release. A spectro-temporal graph of percussiveness is built and then compared to music tracks belonging to the second database.

In some embodiments an automatic content analysis of the sound features of a music track can be performed so that extracted sound features can be classified, segmented and compared. Based on these extracted sound features a sound features vector can be built identifying a personal class. From the general database, an algorithm selects those sounds that are part of the personal class or closely related by means of a music similarity comparison.

Music similarities are herein defined as similarities in terms of value of the parameters characterizing the features of a sound.

Similarities between songs or music tracks may also be defined as similarities between combinations of values of different sound features, which may have different weight. For example, sounds features producing enhanced relaxing effects on the listener may have a weighting factor higher than other features, when evaluating the similarities between songs.

In some embodiments the selection of elements from the second database is based on similarities matching between combinations of sound features.

On the basis of these similarities the songs within the general database are ranked so as to form a playing list of the most similar songs. In some embodiments this playing list is the filtered general database, also referred as filtered second database.

In some other embodiments a certain number of top ranking songs are selected and included in the filtered hospital database, while the lowest ranking are excluded from the filtered hospital database.

For example in some embodiment the top 25 elements of the playing list may be selected. In some other embodiments the top 50 elements of the playing list may be selected. In some other embodiments the bottom 25 elements of the playing list may be excluded from the selection. In some other embodiments the bottom 50 elements of the list may be excluded from the selection.

In some embodiments the second filter comprises a digital signal processing algorithm that, when applied to the first database, determines the sound features of elements in the first database and selects elements from the first database having values of the sound features corresponding to pre-determined values.

The second filter is referred herein also as healing filter. The wording healing is used as referred to its beneficial effect on people who are exposed to these sounds, also referred to as listeners.

The second filter or healing filter may be a digital signal processing algorithm which filters out music with a desired effect on the listeners. For example, if the required effect is relaxation of the listener, the filter selects elements such as sounds or music tracks having features known to be soothing, comforting and calming for the listener. If the required effect on the listener is activation, the filter selects sounds or music tracks having features known to be stimulating for the listener.

This filtering process may be based on the spectro-temporal characteristics of the sound. For example, the digital signal processing algorithm may determine the tempo of the music perceived by the listener, also referred as perceived tempo.

Tempo is a descriptive parameter of music and has been the focus of many systems for automatic music information retrieval, for example, automatic tempo-trackers. Tempo may be distinguished between notated tempo and perceptual tempo.

Perceptual tempo refers to listeners' tempo perception as fast, moderate or slow, while they listen to a piece of music with fairly constant overall tempo. Music perceived to be faster will have higher perceptual tempo than music perceived to be slower.

Perceived tempo is generally measured in beats per minutes, i.e. the perceived number of beats per minute. Generally, listeners tend to prefer tempi within the heart beat tempo, i.e. 120 beats per minute (bpm). For example, music tracks with tempi lower than 80 bpm are known to have a relaxation effect on listeners.

The proposed algorithm may be effective in estimating the perceptual tempo.

Example of the algorithm used for determining the perceived tempo can be based on, for example, a multi-band resonator filter bank, envelope autocorrelation method or inter-onset interval (IOI) histogram method. These methods provide an internal representation of "periodicity energy" as a function of tempo which is an analogous representation of perceived tempo and can be quantitatively compared with perceived-tempo histograms.

Determination of perceived tempo can also be derived from the tapping to the beat of listeners and the generated histograms of perceived tempi for each music track produced by all the listeners.

The selection of elements from the first database is based on the matching between the values of the sound features of the elements in the first database, which have been determined and pre-determined values.

Pre-determined values of perceived tempo are related to the effect that one wants to achieve on the listener.

In some embodiments the selection of elements from the first database is based on the matching between combinations of sound features having desired pre-determined values.

For example it may be that a specific combination of values of perceived tempo, tonality and spectral bandwidth is the combination of pre-determined values that are desirable in order to produce a relaxing effect on a listener. In this case the selection of elements from the first database will be based on the best matching of the combination of those sound features. In some embodiments a ranking of elements from the first database will be produced based on the level of matching between the desired combination of pre-determined values and the values of the sound features of the elements. In this way elements are ranked into a list and parameters for selecting elements can be tuned as desired. For example, in some embodiment the top 25 elements of the list may be selected. In some other embodiments the top 50 elements of the list may be selected. In some other embodiments the bottom 25 elements of the list may be excluded from the selection. In some other embodiments the bottom 50 elements of the list may be excluded from the selection.

In some embodiments the preferred values of sound features are further determined by: exposing a listener to elements from the personalized sounds database; monitoring variations of at least one physiological condition of the listener during the exposure to the elements; extracting the preferred values of sound features from the elements of the personalized sounds database to which the listener is exposed to, when the at least one physiological condition of the listener have a pre-determined magnitude.

In some embodiments a listener may provide a feed-back to further optimize the personalization of the personalized sounds database. The feed-back may be used for further iteration in the selection of elements from the second or general database. This is achieved by further determining the preferred sound features used for creating the first or personal filter as to create a fine tuned personal filter. The fine tuned personal filter, once applied to the second or general database, selects, from the second or general database, those elements having features with values similar to the updated preferred values of sounds feature. This iteration may be repeated several times as based on the different feed-back of a listener which in turn determines updated preferred sound features used to update and fine tune the personal filter.

The feed-back from a listener is therefore obtained by exposing this listener to the personalized, i.e. improved sound database and by monitoring his physiological condition.

The physiological conditions of a listener, while he is exposed to the database, i.e. he listen to the personalized database of sounds, are monitored to determine if variations of physiological conditions related to the desired effect occur during the exposure.

Physiological condition may be stress or relax, indicated by physical changing in body parameters related to it.

Example of physiological condition variations are variations in the vital signs such as the changing in the heart beats rate, variation of the electrical activity of the brain or variation in skin conductance. These variations can be measured by any device able to appreciate quantitative variation of these vital signs.

For example, if a patient is exposed to the personalized database of sounds and its brain activity is recorded through a Electroencephalography (EEG), variation of the brain rhythmic activity, such as in the alpha wave range (8-12 Hz) may be an indication that the values of the sound features of the music track that the patient is listening to, should enter the preferred values of sound features used for creating the personal filter.

Magnitude is here defined as level of a vital sign, which can be measured in the body of the listener.

Pre-determined magnitude is defined as the level of a vital sing or a combination of vital signs that are known to correspond to the desired effect on the physical condition of the listener.

For example if the listener is stressed and a state of relaxation is the condition that is to be achieved, the pre-determined level of skin conductance is the level that correspond to a state of relaxation of the listener.

For example, if the desired effect on the listener is relaxation and the listener heart beat rate decreases upon exposure to a particular music track in the personalized sounds database, the values of the sounds feature of this music track, such as tonality, percussiveness and spectral bandwidth, are extracted. These values are used as preferred values in applying the first filter, i.e. the personal filter, to the second database, e.g. a music library of a hospital. In this way the preferred values of sound features in the first database, e.g. the personal database are updated. These updated preferred values are used for selecting from the second database, those sounds having features with values similar to the updated preferred values of the sounds feature of the first database.

In some other embodiments the extracted values are used as preferred values in applying the second filter, i.e. the healing filter, to the first database, e.g. the personal database. In this way the characteristics of the sounds producing healing effects in the second filter are updated.

These updated characteristics are used for selecting from the first database, those sounds having characteristics similar to the updated characteristics of the sounds producing healing effects in the second filter.

An optional closed-loop feedback system is therefore established and the personalized database can further be personalized and optimized through the monitoring of the effect of the different music tracks on the patient and by adapting the music selection accordingly.

In one embodiment a second database is not present. The invention is therefore limited to the application of a first filter, i.e. healing filter, to a first database. This first database may a music library, for example belonging to a patient of a hospital or provided by the family of the patient of a hospital on behalf of the patient. The first filter may be a digital signal processing algorithm, which determines values of the perceived tempo of the sounds in the first database and selects sounds from said first database corresponding to pre-determined perceived tempo values.

The pre-determined values correspond to values which cause the modification in physiological condition of a listener associated to change of mood, e.g. happiness or sadness, or physical state, stress or relaxation which are desired. For example, the appropriate healing effects may be relaxing in case the patient is stressed, or arousing in case the patient needs to be activated.

This processing is based on the spectro-temporal characteristics of the sound. The result is a filtered patient collection.

In some other embodiments the computer-implemented method according to the first aspect of the invention further comprises, exposing a listener to the elements from the personalized sounds database.

In some embodiments the computer-implemented method further comprises: monitoring variations of at least one physiological condition of the listener during the exposure to the elements; removing from the personalized sounds database elements producing undesired variations of at least one physiological condition of the listener during the exposure to the elements.

In some embodiments the fine tuned personal filter may be applied to the personalized sounds database so as to remove the music tracks which are not providing the desired effect on the physiological condition of the listener.

In some further embodiments the first or personal filter may be applied to a combination of the filtered first database and filtered second database.

In a second aspect the invention relates to a computer based system for producing a personalized sounds database comprising: at least one electronic data processor; a data communication interface connected to the data processor; and wherein the computer based system is configured to: determine preferred values of sound features of elements of a first database comprising elements, such as sounds, thereby creating a first filter; and apply the first filter to a second database comprising elements, such as sounds, thereby producing a filtered second database.

In some embodiments according to the second aspect of the invention, the computer based system is further configured to apply a second filter to a first database comprising elements, such as sounds, thereby producing a filtered first database.

In some other embodiments according to the second aspect of the invention the computer based system is further configured to combine the filtered first database with the filtered second database, thereby providing the personalized sounds database.

In a third aspect the invention relates to a computer-readable storage medium having stored therein computer readable instructions, which, when loaded in and executed by a computer causes a computer to perform the steps as defined by the first aspect of the invention and its embodiments.

The basic idea of the invention relates to the realization of a personalized database of sounds containing healing sounds.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings.

DESCRIPTION OF EMBODIMENTS

Figure 1:
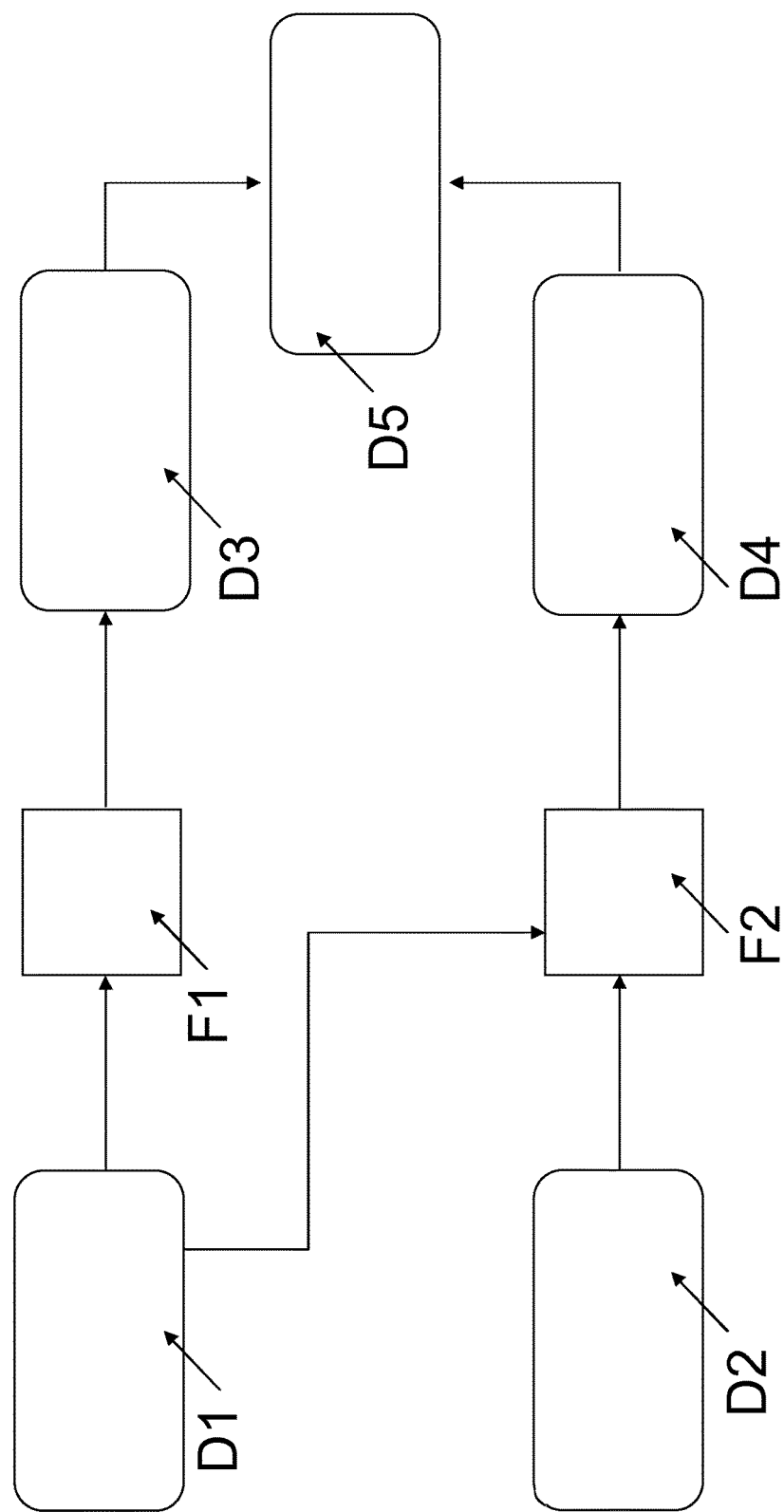
FIG. 1 is a schematic illustration according to one embodiment of the invention.

An embodiment of the invention is illustrated in FIG. 1.

A personal database comprising sounds, D1 is processed though a healing filter, F1. F1 selects the sounds and/or music tracks features from the personal database D1, which are known to produce desired effects on listeners. In this way a filtered personal database D3 is produced.

A hospital database comprising healing sounds D2 is processed through a personal filter, F2. F2 determines the preferred sound features of the personal database D1. When the filter F2 is applied to the hospital database D2, F2 selects from the hospital database D2 those sounds, which are closely related, by means of sounds features similarity, to the preferred sounds features of the personal database D1. In this way a filtered hospital database D4 is produced. By combining filtered personal database D3 and filtered hospital database D4 a new database D5 is produced.

Figure 2:
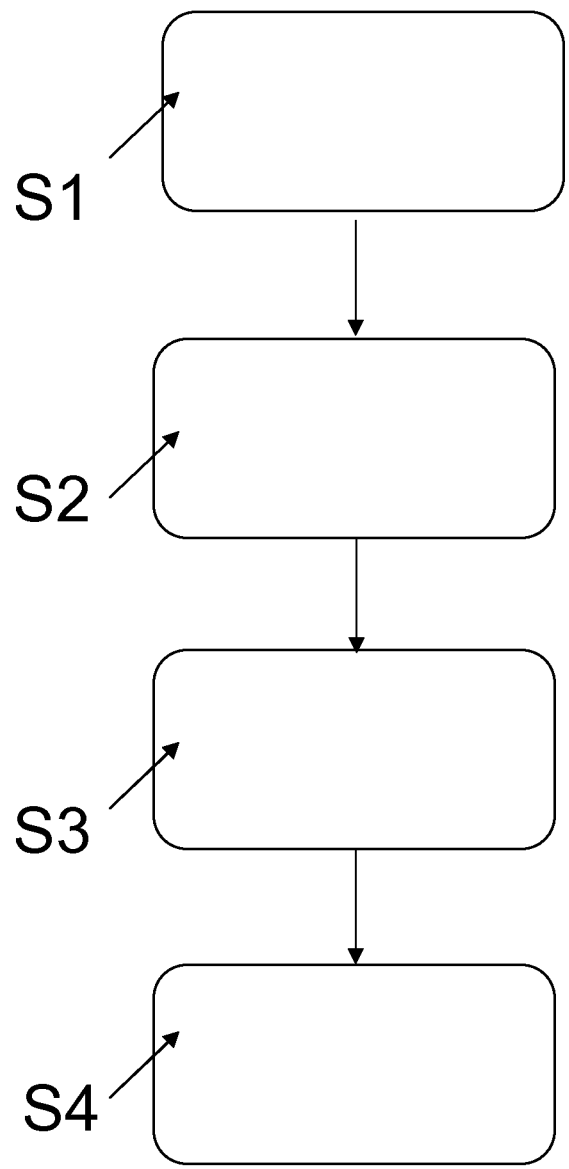
FIG. 2 is a flow-chart of a method according to one embodiment of the invention.

FIG. 2 is a flow-chart of a method according to one embodiment of the invention. In this embodiment the method comprises the following steps:

S1, determining preferred values of sound features of elements of a first database D1, thereby creating a personal filter (F2);

S2, applying the personal filter F2 to a hospital database D2, thereby producing a filtered hospital database D4;

S3, applying a healing filter F1 to a personal database D1, thereby producing a filtered personal first database D3;

S4, combining the filtered personal database D3 with the filtered hospital database D4, thereby providing a personalized sounds database D5.

In some embodiments the personalized sounds database is obtained by applying a healing filter to a personal database, such as a collection of sounds and/or music tracks. The personal database comprises a collection of sounds and/or music tracks which for example belongs to a patient of a hospital and may be provided by himself or his relatives. The healing filter determines the sounds and/or music tracks features which are known to produce desired effects on listeners. For example the healing filter may be tuned to determine sounds and/or music tracks having features which are known to produce relaxing effect on the listeners. A filtered personal database containing a collection of personal sounds and/or music tracks having the characteristic of producing a desired effect on the listener is therefore obtained by applying the healing filter.

In some embodiments, when the method is applied in relation to treatment of patients of a hospital, the method applies at least two filters: a healing filter, also referred to as second filter to a personal databases such as a collection of sounds and/or music tracks, also referred to as first database, thereby providing a filtered personal database; a personal filter, also referred to as a first filter to a hospital database, such as a hospital collection of sounds and/or music tracks, also referred to as second database, thereby providing a filtered hospital database.

The hospital database comprises a collection of sounds and/or music which is known to produce desired effects on listeners. For example the collection may comprise music tracks which are known to produce relaxing effect on the listeners.

In some other embodiments the personal collection may be not accessible, e.g. in case of acute treatment of patients. A personalized filter is therefore obtained by determining preferred values of sounds features of elements of a patient database which is produced by relatives or friends of the patient. For example relatives, friends, colleagues, acquaintances or people who know the music taste of the patient, e.g. in terms of genre, mood and tempo, may create a patient database by choosing music tracks or sound from music library, such as their own or the hospital collection.

In some other embodiments the method further combines the two filtered databases, thereby providing an improved database, also referred as to personalized database.

This invention describes also a method to personalize a sounds database by combining at least two filtered databases so as to produce a personalized and therefore improved database of sounds.

In some embodiments, when the method is applied in relation to treatment of patients of a hospital, the first database may be a personal music collection and the second database may be a hospital music collection.

The combination of the personal music collection which has been filtered through the healing filter and the hospital music collection which has been filtered though the personal filter produces a music collection having healing effect on the listener which preserves the personal sounds characteristics of the personal music collection.

For example songs from the filtered personal collection having perceived tempi producing relaxing effects on the listeners and sounds from the filtered hospital collection having sounds features, e.g. tonality, percussiveness, spectral bandwidth, similar to the sounds of the songs in the personal database may be combined to produce the personalized sounds database.

The combination of the filtered collection may be done by simple addition of the songs therein contained into a playing list, being said playing list the personalized database.

In some other embodiments the songs belonging to the two filtered databases may have different weight assigned on the basis of the final characteristic of the personalized collection.

For example, a personalized collection having relaxing effect on the listener may be produced by combining songs from the filtered personal collection and filtered hospital collection having a high weighting factor due to their relaxing character. Songs with a lower relaxing character may be excluded from the combination due to their low weighting factor.

Favorite sounds may be easily identified by user with his/her own collection of sounds on the basis of the desired effect the user wants to achieve.

For example if the listener would like to relax he may choose a collection of music tracks which are his favorite in light of the relaxing state he would like to achieve. This may include soft tunes, slow tempi. Alternatively a different favorite collection may be preferred is an active state would like to be achieved. This may include high tempi.

Favorite elements may be personally chosen or chosen by relatives with a personal database or within other databases, for example the hospital database.

In some embodiments when the method is applied in relation to treatment of patients of a hospital the first filter or personal filter may be a digital signal processing algorithm which determines the musical preferences of the patient from the characteristics of the patient collection and filters out the sounds having similar musical preferences from the hospital database. With this filter, a personalized selection among the hospital collection of healing sounds is made.

For example, for each sound of the database, e.g. for each song in the patient collection, sound features, such as genre, tonality, percussiveness, rhythm and spectral bandwidth, are determined. For example an automatic content analysis of the sound features of a music track can be performed so that extracted feature can be classified, segmented and compared. Based on these feature vectors, a personal class is built. From the hospital collection, an algorithm selects those sounds that are part of the personal class or closely related by means of a music similarity comparison.

On the basis of these similarities the songs within the hospital collection are ranked so as to form a playing list of most similar songs.

In some embodiments this playing list is the filtered hospital database.

In some other embodiments a certain number of top ranking songs are selected and included in the filtered hospital database, while the lowest ranking are excluded from the filtered hospital database.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of producing a personalized sounds database comprising:
    determining preferred values of sound features of elements of a first database comprising elements of sound, thereby creating a first filter, wherein the first database is a personal database of a patient of a hospital, the sound features are sound features preferred by the patient, and the sound features are determined through automatic content analysis;
    applying said first filter to a second database comprising elements of sound, thereby producing a filtered second database, wherein the second database is a hospital database of healing sounds known to produce desired effects on listeners, and the filtered second database include only sounds having the preferred values of sound features of elements of the personal database;
    applying a second filter to the first database comprising elements of sound, thereby producing a filtered first database including only a collection of personal sounds having a characteristic of producing a desired effect on the patient;
    combining said filtered first database with said filtered second database, thereby providing said personalized sounds database; and
    playing the sounds provided on the personalized sounds database to the patient, thereby eliciting the desired effect on the patient.

2. The computer-implemented method according to claim 1, wherein said first database is a database comprising user favorite sounds.

3. The computer-implemented method according to claim 1, wherein said first filter comprises a digital signal processing algorithm, said digital signal processing algorithm, when applied to said second database, selects, from said second database, those elements having features with values similar to said preferred values of said sound features of said elements of said first database.

4. The computer-implemented method according to claim 1, wherein said sound features are tonality, percussiveness, and spectral bandwidth.

5. The computer-implemented method according to claim 1, wherein said second filter comprises a digital signal processing algorithm, said digital signal processing algorithm, when applied to said first database, determines said sound features of elements in said first database and selects elements from said first database having values of said sound features corresponding to pre-determined values.

6. The computer-implemented method according to claim 1, wherein said sound features are the perceived tempo of the elements.

7. The computer-implemented method according to claim 1, further comprising,
    exposing a listener to said elements from said personalized sounds database.

8. The computer-implemented method according to claim 1, wherein said preferred values of sound features are further determined by:
    exposing a listener to elements from said personalized sounds database;
    monitoring variations of at least one physiological condition of said listener during the exposure to said elements;
    extracting said preferred values of sound features from the elements of said personalized sounds database to which said listener is exposed to, when said at least one physiological condition of said listener have a pre-determined magnitude.

9. The computer-implemented method according to claim 7, further comprising:
    monitoring variations of at least one physiological condition of said listener during the exposure to said elements;
    removing from said personalized sounds database elements producing undesired variations of at least one physiological condition of said listener during the exposure to said elements.

10. A computer based system for producing a personalized sounds database comprising:
    at least one electronic data processor;
    a data communication interface connected to said data processor;
    wherein said computer based system is configured to:
        determine, through automatic content analysis, preferred values of sound features of elements of a first database comprising elements of sound, thereby creating a first filter, wherein the first database is a personal database of a patient of a hospital, and the sound features are sound features preferred by the patient;
        apply said first filter to a second database comprising elements of sound, thereby producing a filtered second database, wherein the second database is a hospital database of healing sounds known to produce desired effects on listeners, and the filtered second database include only sounds having the preferred values of sound features of elements of the personal database,
        apply a second filter to a first database comprising elements of sound, thereby producing a filtered first database including only a collection of personal sounds having a characteristic of producing a desired effect on the patient,
        combine said filtered first database with said filtered second database, thereby providing said personalized sounds database; and
        play the sounds provided on the personalized sounds database to the patients, thereby eliciting the desired effect on the patient.

11. A computer-readable storage medium having stored therein computer readable instructions, which, when loaded in and executed by a computer causes a computer to perform the steps as defined by the method in claim 1.

12. The computer-implemented method according to claim 1, further comprising:
wherein combining said filtered first database with said filtered second database includes weighting a first sound in said filtered first database having a higher healing character than a second sound in said filtered first database with a first weight and weighting the second sound with a second weight, wherein the first weight is greater than the second weight.

13. The computer-implemented method according to claim 1, further comprising:
selecting sounds from the second database based on similarities matching between combinations of sound features; and
ranking, based on the similarities, the sounds within the second database to form a play list of the most similar songs.

14. The computer-implemented method according to claim 13, further comprising:
selecting a pre-determined sub-set of the sounds within the second database based on the ranking.

15. The computer-implemented method according to claim 1, further comprising:
selecting sounds from the first database based on a matching between combinations of sound features having desired pre-determined values.

16. The computer-implemented method according to claim 15, wherein the combination is a pre-determined combination of values of tempo, tonality and spectral bandwidth which produce a relaxing effect on a listener.

17. The computer-implemented method according to claim 1, further comprising:
monitoring at least one physiological signal of the patient to determine a healing sound that produces a desired effect on the patient.

18. The computer-implemented method according to claim 1,
wherein the at least one physiological signal includes at least one of brain activity or heat beat rate.

19. The computer-implemented method according to claim 1, further comprising:
wherein playing the sounds includes randomly playing the sounds.

20. The computer-implemented method according to claim 1, further comprising:
wherein playing the sounds includes playing the sounds with a pre-determined order.

* * * * *